United States Patent

Remes et al.

[11] Patent Number: 5,361,775
[45] Date of Patent: Nov. 8, 1994

[54] METHOD FOR DETERMINING MUSCLE ENDURANCE AND SENSITIVITY TO FATIGUE

[75] Inventors: Arto J. Remes; Kari U. Eskelinen, both of Kuopio, Finland

[73] Assignee: MEGA ELEKTRONIIKKA OY PL., Kuopio, Finland

[21] Appl. No.: 42,782

[22] Filed: Apr. 6, 1993

[51] Int. Cl.$^5$ ............................................. A61B 5/0488
[52] U.S. Cl. .................................... 128/733; 128/781; 128/782
[58] Field of Search ................. 128/733, 774, 781–782

[56] References Cited

U.S. PATENT DOCUMENTS

| | | | |
|---|---|---|---|
| 4,611,284 | 9/1986 | McGill et al. | 128/733 X |
| 4,664,130 | 5/1987 | Gracovetsky | 128/733 X |
| 5,086,779 | 2/1992 | DeLuca et al. | 128/733 |

Primary Examiner—Angela D. Sykes
Attorney, Agent, or Firm—Cushman, Darby & Cushman

[57] ABSTRACT

The object of the invention is a method for determination of endurance and sensitivity to fatigue of a muscle. In this method one or more recording electrodes are placed on top of the muscles to be tested from the test subject and the action potentials of the muscle cell membrane of a muscle are measured by recording electrodes and equipments. It is difficult to define the endurance and sensitivity to fatigue of a person's muscles in comparison with the general population. In the method according to the invention a frequency analysis, the so-called FFT-analysis, is performed to the recorded EMG-signal, and by using this analysis with three or more calculation parameters the lowering of the conduction rate of a muscle cell membrane is observed as well as the rate of change of the calculation parameters as a function of time, and a comparable value is obtained which indicates the endurance and sensitivity to fatigue of a muscle. The obtained values are compared with an index which is normalized for each muscle test, and this gives the muscle condition of the person tested in comparison with the general population, or the results are compared with the values previously measured for the individual, and the results are presented graphically.

6 Claims, 5 Drawing Sheets

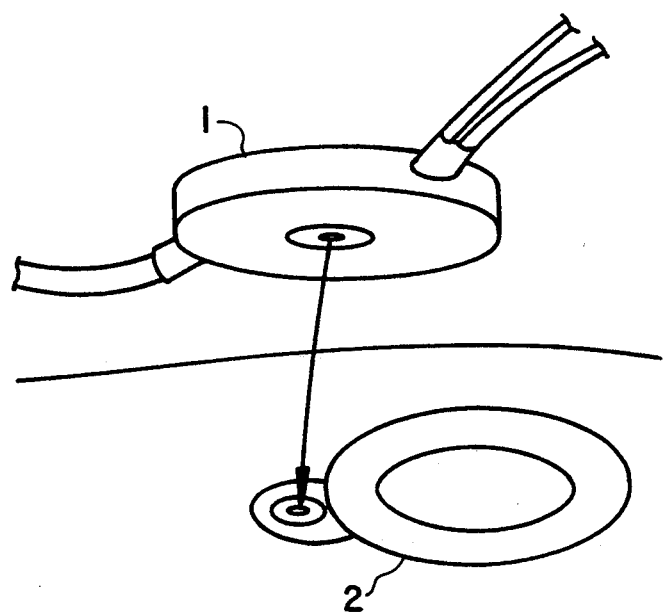
FIG. 2
FIG. 4
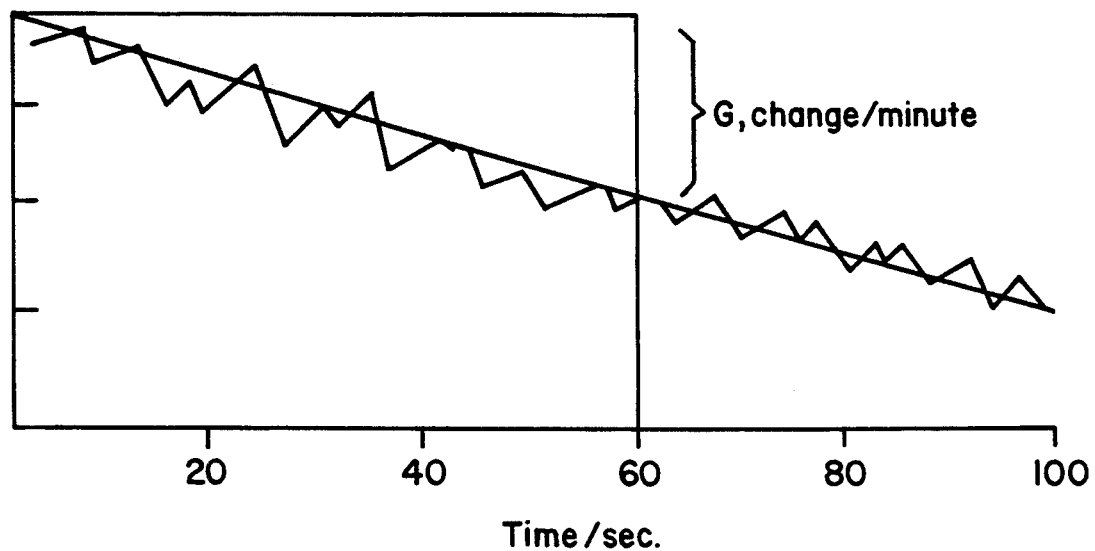

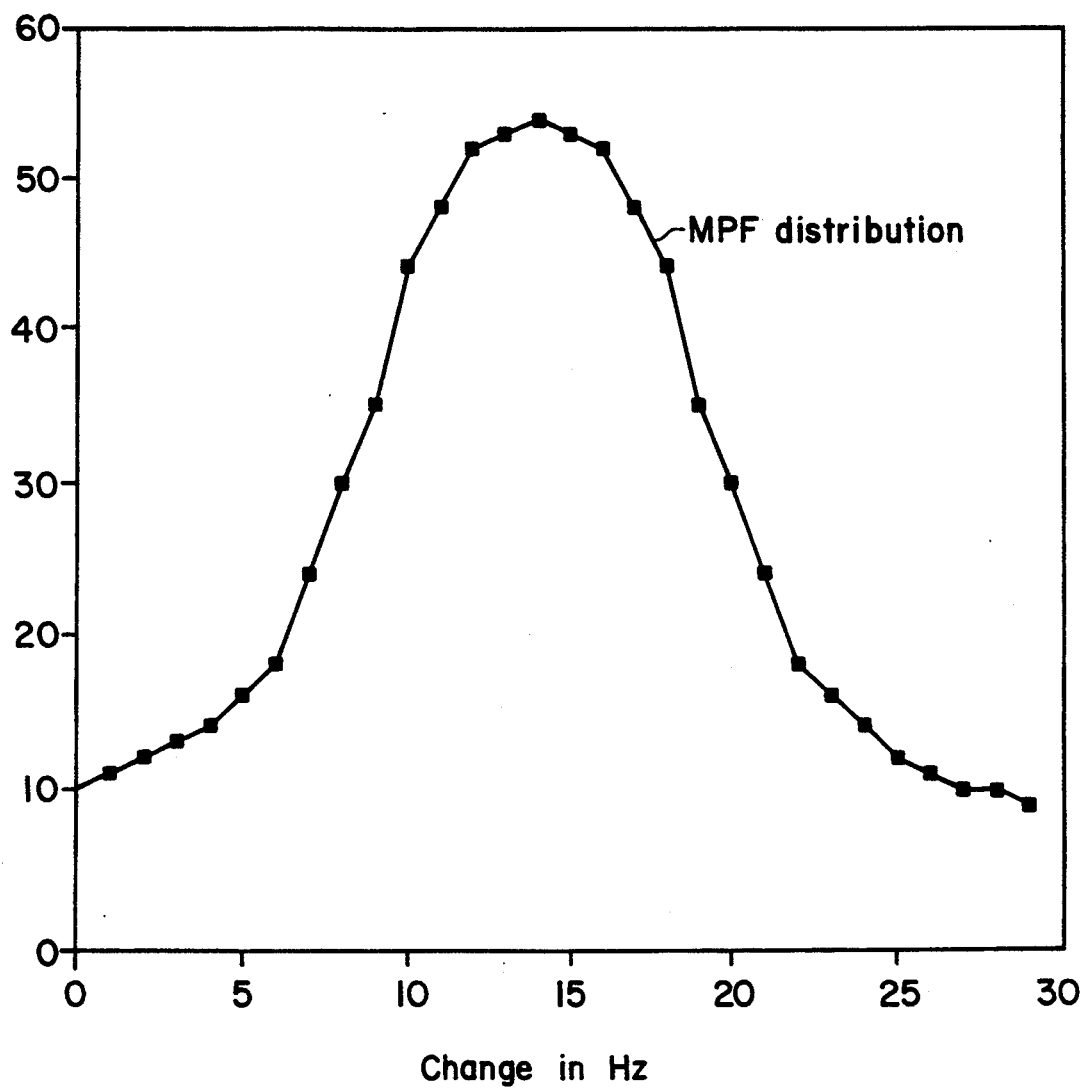

METHOD FOR DETERMINING MUSCLE ENDURANCE AND SENSITIVITY TO FATIGUE

FIELD OF THE INVENTION

The present invention relates to a method for determining muscle endurance and sensitivity due to fatigue.

BACKGROUND OF THE RELATED ART

The condition of the muscles in the human body greatly affects a person's quality of life, efficiency at work, contentment and many other things. When measuring muscle condition, a good standard is a comparison with the general population of the same age. Muscle condition, that is the endurance and fatigue of muscles, can be determined using different kinds of tests, but those known in the art do not give direct and quick reliable results or reliable results for comparison, for instance, with the general population.

Muscles consist of muscle fibers, that is, muscle cells. A single nerve fiber regulates many muscle fibers. Muscle fibers divide into myofibrils and again into myofilaments which divide into actin and myosin filaments. Muscular contraction occurs mechanically in these micro units due to the entry of Ca++-ions with subsequent hydrolysis of adenosine triphosphate (ATP). Muscular contraction is caused by a nerve impulse which releases Ca++-ions from cytoplasm into myofibrils, and this causes actin and myosin filaments to slide into contact with each other. Simultaneously, the action potential proceeds on the muscle cell membrane, thus causing a parallel phenomenon in millions of actino-myosin units.

Many muscle cells form functional units which are called motor units. When muscle strength has to be increased, more motor units are recruited into the contraction process.

The action potentials involved can be measured and are measured electrically from inside the muscle cell, for instance by using needle electrodes (needle electromyography, needle EMG) or surface electrodes (surface EMG). Motor units, that is actino-myosin units, function at different frequencies and are stimulated at different times. Thus an EMG-signal of a contracting muscle, recorded for instance at the skin surface, contains frequency components mainly in the frequency range of 10–400 Hz. The intensity of the recording signal varies in this case from a few micro volts ($\mu V$) to about 5000 $\mu V$. This kind of measurement and observation of muscles is very common and the results are used for different purposes.

Muscular contraction obtains its energy from ATP. Oxygen is important for both synthesis of the ATP and its catabolism. During heavy muscle work, as a result of the breakdown of ATP, many hydrogen ions are formed inside the muscle cell which do not bind to other chemical reactions with oxygen. Thus the acidity of cytoplasm increases, the production of energy decreases and the muscle begins to fatigue. As the muscle cell becomes acidic, the conduction rate of the muscle cell membrane diminishes and the formation of an action potential in the muscle cell slows down and the penetration of nerve impulses into the muscle cell is inhibited. This phenomenon can be detected with present-day measuring devices.

SUMMARY OF THE INVENTION

The aim of the invention is to bring forward a method for analyzing and determining muscle endurance and sensitivity due to fatigue quickly and reliably and which computer compares the results with the general population. Furthermore, the aim of the invention is to bring forward a method which can be applied in the follow-up of an individual's muscle condition.

The aim of the invention is achieved with the method characterized in the appended claims.

According to the invention, the reduction in the conduction rate of a muscle membrane and the slowing down of a formation of the action potential can be utilized in determining the muscle endurance and sensitivity to fatigue by performing a frequency analysis (FFT-analysis) of a recorded EMG-signal. By using the analysis with three or more calculation parameters (MF=median frequency, MPF=mean power frequency and ZCR=zero crossing rate), the reduction in the conduction rate on a muscle cell membrane can be observed. In these calculation parameters:

The power spectrum of a continuous signal can be defined by the formula $S(f) = Re^2 + Im^2$
In which,
  $S(f)$ = power spectrum
  $Re$ = real term
  $Im$ = imaginary term
The amplitude spectrum is defined by:

$$A(f) = \sqrt{S(f)} = \sqrt{Re^2 + Im^2}$$

The median frequency (MF) indicates the frequency at which the spectrum is divided into two equal areas according to the following:

$$\int_0^{MF} S(f)df = \int_{MF}^{\infty} S(f)df = \frac{1}{2}\int_0^{\infty} S(f)df$$

The mathematically mean power frequency is defined by the following:

$$MPF = \frac{\int_0^{\infty} fS(f)df}{\int_0^{\infty} S(f)df}$$

In a discrete form, the same formula is:

$$MPF = \frac{\sum_{i=1}^{\infty} f_i A_i}{\Delta f \sum_{i=1}^{\infty} A_i}$$

The zero crossing rate (ZCR) indicates the number of zero crossings in an EMG signal/sec.

An averaged EMG is calculated according to following formula:

$$\text{AVERAGED INTEGRATED } EMG = \frac{\int_0^{1023} /\text{rawdata}/}{1024}$$

When examining the rate of the change of MF, MPF and ZCR parameters as a function of time, for example per minute (Hz/min), a number which can be used in comparisons is obtained which describes muscle endurance and sensitivity to fatigue.

By applying the described phenomenon and calculation in the follow-up of patients in physiotherapy and training, a normalized index can be produced for each muscle test. This can be, for example, by age group for males and females. By using this index, the muscle condition of a person is obtained directly by a comparison with the general population. The described method also allows a follow-up of the progress of the muscle condition at an individual level. Thus the method according to this invention can be applied in a follow-up to training, evaluation of the ability to work, choosing the right exercises for training and muscle condition and in an evaluation of preventive measures for back/neck problems in the workplace or elsewhere.

BRIEF DESCRIPTION OF THE DRAWINGS

In the following, the invention will be explained in more detail by referring to the attached drawings, in which:

FIG. 2 shows a recording amplifier used in this method and its installation on the skin, FIG. 4 shows the determination of fatigue index on the MPF-diagram, FIG. 5 shows the deviation of the MPF-index.

DESCRIPTION OF THE PREFERRED EMBODIMENTS

Figure 1:
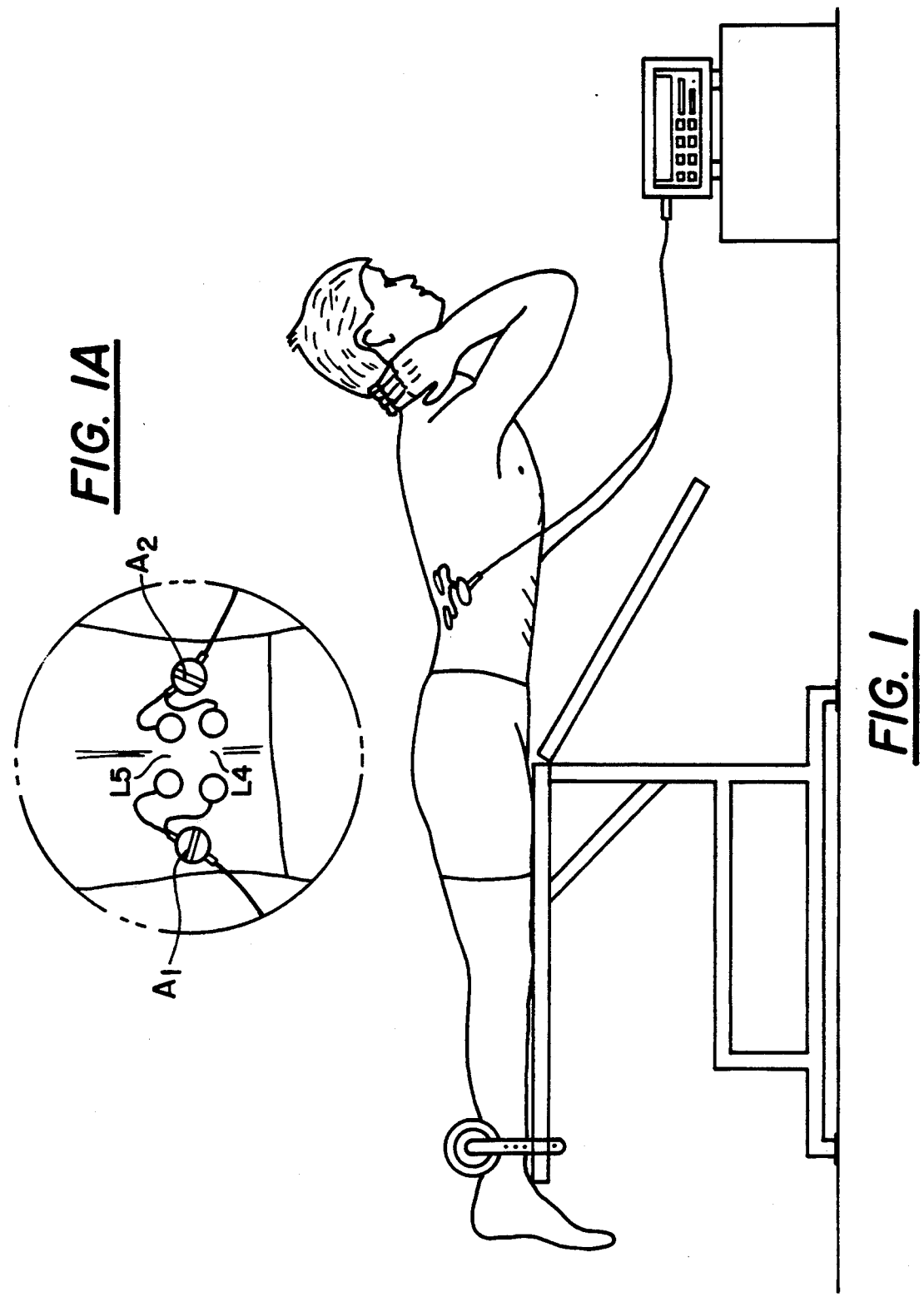
FIG. 1 shows a side view of an embodiment for performing the measurement according to the method.

In an embodiment according to FIG. 1 muscle condition is measured as the person to be tested lies on a treatment table horizontally without support. The hip is supported from the top part of the iliac downwards. The person holds the upper body in this position for example for 30-60 seconds. The horizontal level can be checked in a suitable way, for instance by a plumb line which is hanging above the person and lightly touches the back. For comparison, the horizontal level of the treatment table can also be used. It is important that the person's position stays constant during the measurement. Recording electrodes A1 and A2 are attached on the skin surface at the top of the erector spinae muscles, both on the right and the left side at the level of lumbar vertebrae L4-L5 about 3-5 cm from the spine bipolarly.

According to FIG. 2, EMG recording amplifiers 1 have been placed on a knob which is to be fastened a grounded electrode 2. It is essential to place the amplifiers directly on the skin surface to absorb common-mode disturbances. The properties of the recording amplifiers in this embodiment are as follows:

Gain: 500
CMRR > 130 dB
Frequency band: 20-470 Hz (3 dB points)
Input impedance: $10^{12}$ ohm
Type: Differential Parameters connected with registration are chosen on the keyboard of the recorder. During the test, an EMG signal is recorded in the memory of the registration device, for example 1000 recordings per second, When the test is completed, the recorded data is transferred for example by an optical data transfer to a computer for analysis and normalization.

Figure 3:
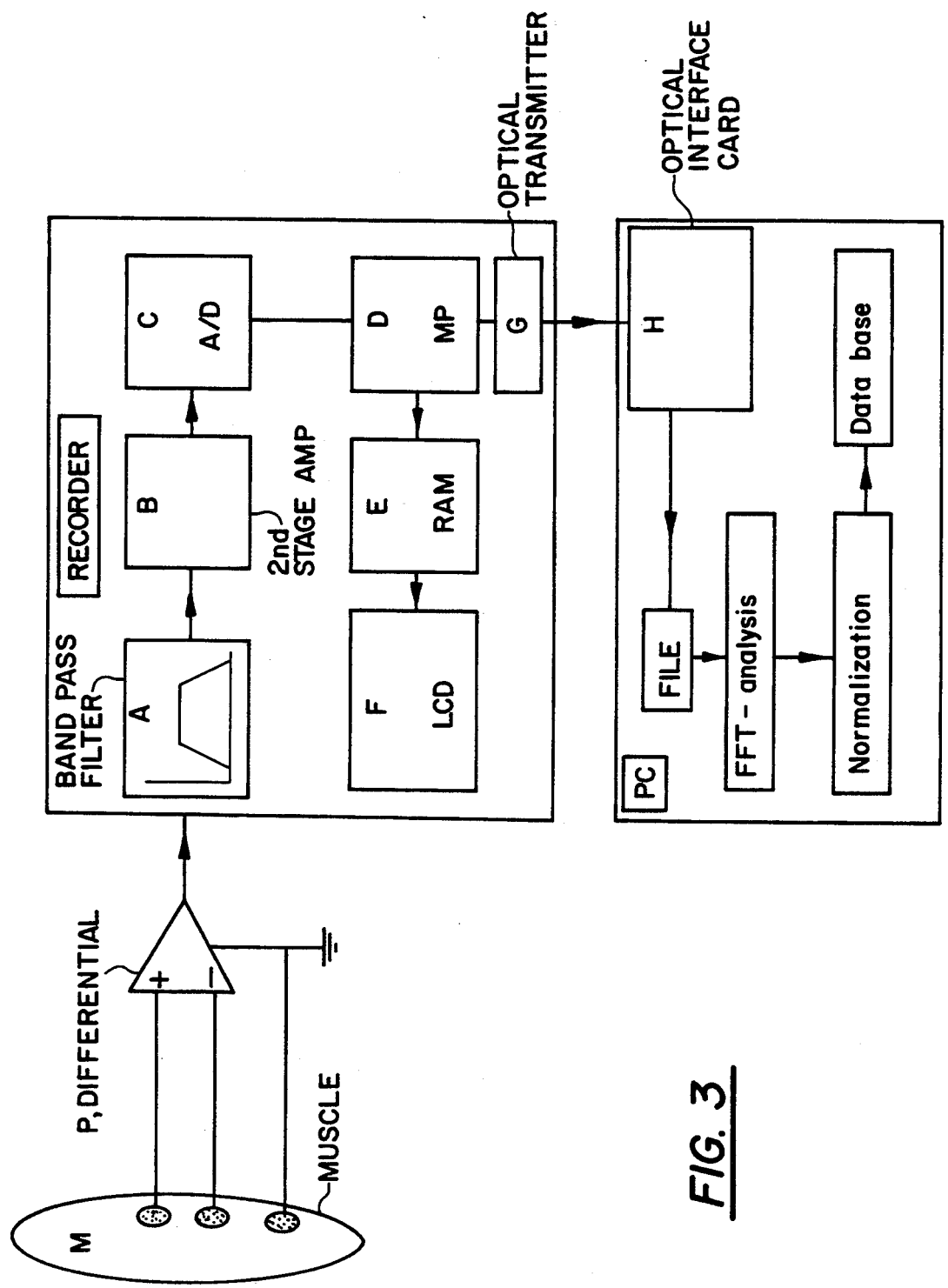
FIG. 3 shows a schematic representation of a recording system used in the method according to the invention.

A recording system used in the method is presented in FIG. 3. Ag/AgCI disposable surface electrodes, which have been placed on the surface of the skin, register motor unit potentials which are activated in the muscle M under the electrodes. Common-mode disturbance (60 Hz, ECG) connected with both inputs is excluded by using a differential preamplifier P and bipolar recording. Thereafter the signal is filtered through a band pass filter A, 5-470 Hz. The filter has been obtained by using a previously known operational amplifying technique. From the second stage amplifier B, the signal is provided to a 12-bit analog-to-digital converter C where the signal is converted to a readable form, for example 1000 or 2000 recordings a second, and provided to the microprocessor D. The modified values can be processed mathematically by a microprocessor D or stored directly in a RAM memory E.

The programming of the recorder is guided by an LC-display F. The data recorded in the memory is transferred to a PC computer through the optical transmitter, G. Connected between the optical transmitter G and the optical interface card H, installed in the computer, is an optical fiber cable along which data is transferred using infra red light.

When recorded data has been received, the program creates a file on a hard disc. An operator feeds in data concerning the person to be tested and the names of the muscles measured which are added to the respective data file. The recorded EMG signal is checked on the PC display. When the quality of the signal has been certified, a Fatigue-analysis is started.. It is carried out as follows:

Successive Fourier transformations are calculated on a 1024 points' window over the entire recording signal. A spectrum window is devised such that successive calculation windows are 50% overlapping. From this each of the following spectrum parameters are calculated: Median Frequency (MF), Mean Power Frequency (MPF), Zero Crossing Rate (ZCR) and Averaged EMG (AEMG).

A minute index (FI=fatigue index) describing the endurance/condition of a muscle is calculated by using the following formula:

$$FI = \frac{\text{Change in frequency parameter}}{\text{Duration of test in minutes}}$$

FIG. 4 shows how to determine the fatigue index on an MPF diagram. The extent of change per minute is indicated by the letter G.

The results obtained are classified by age groups and sexes as follows: The population is assumed to behave according to a Gaussian distribution, and FIG. 5 shows the deviation of the change in the MPF parameter in females, 35-45 years of age, in a shoulder muscle fatigue test. The Mean and standard deviation (Mean ±SD) are calculated from the data of a person to be tested. Five classes are obtained from both sides of the mean plus two SDs. The obtained results are compared with the database and the normalized results are printed per channel in the table.

Figure 6:
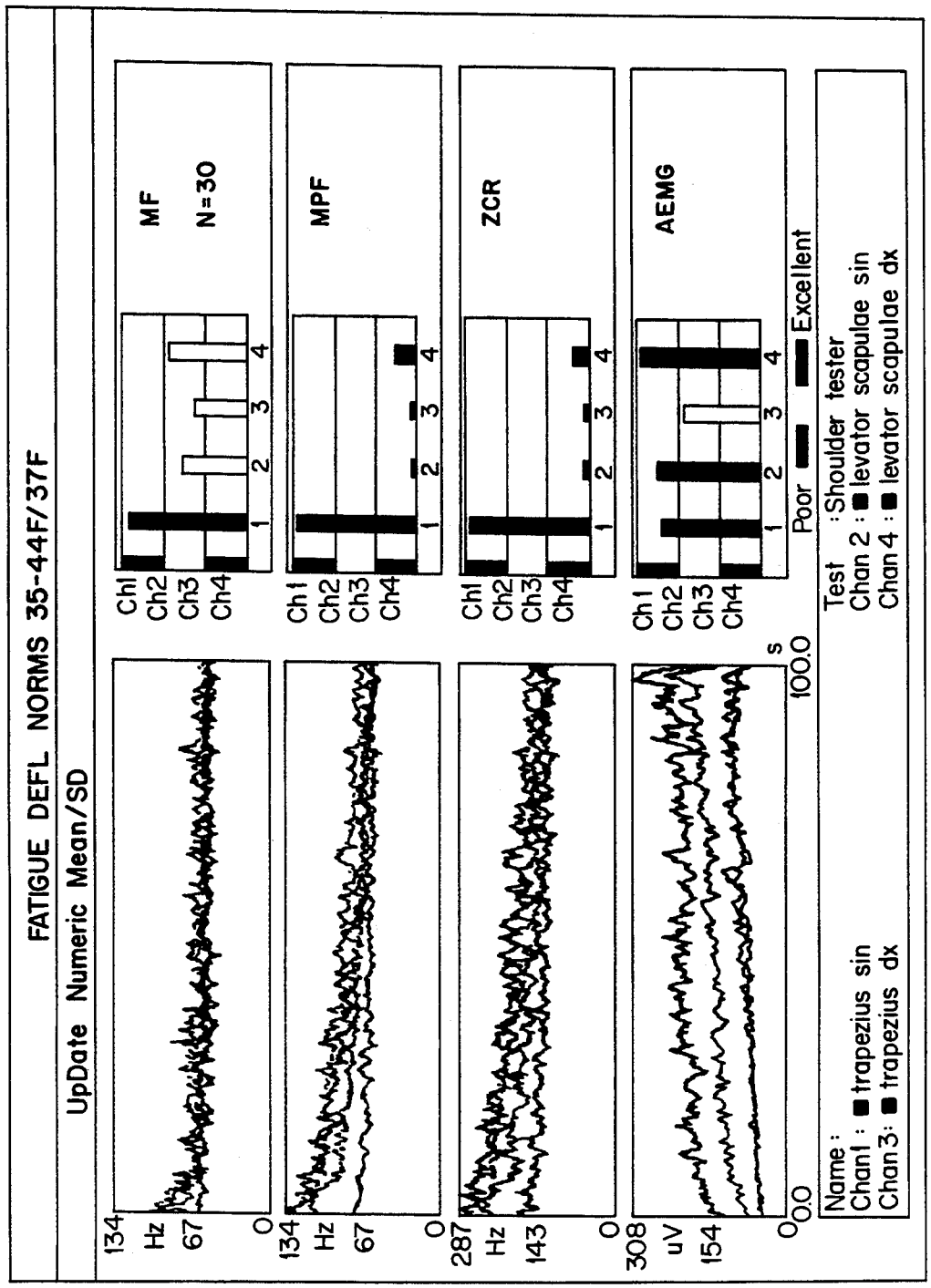
FIG. 6 shows a printout according to the invention which is applicable in a clinical interpretation.

FIG. 6 shows a printout in a shoulder muscle test applicable in a clinical interpretation. The figures show curves indicating the change and fatigue of a muscle.

The results are shown as columns which show immediately the endurance and sensitivity to fatigue of a muscle in comparison with the general population. The classified histograms per channel can be interpreted, for example, by the use of a color code.

What is claimed is:

1. A method for a determination of endurance and sensitivity to fatigue of a muscle comprising:

attaching a grounded recording electrode directly on a skin surface on top of said muscle;

connecting a recording amplifier to said grounded recording electrode;

measuring action potentials of muscle cell membranes of said muscle with said recording electrode;

recording said action potential measurements as EMG data in a memory;

transferring said EMG data through an optical data means to a computation means for analysis and normalization;

performing an FFT frequency analysis on said transferred EMG data using three or more calculation parameters for determining a reduction in said conduction rate of said muscle cell membranes;

obtaining a rate of change value of said calculation parameters as a function of time thereby indicating an amount of said endurance and sensitivity to fatigue of a muscle;

comparing said rate of change value with a normalized index; and presenting a result of said comparison graphically.

2. A method according to claim 1, wherein said three calculation parameters are:

MF (median frequency);

MPF (mean power frequency); and

ZCR (zero crossing rate).

3. A method according to claim 2, further comprising as a calculation an AEMG (averaged EMG) parameter.

4. A method according to claim 1, wherein said normalized index comprises data predetermined to be of an average person in general population.

5. A method according to claim 1, wherein said normalized index comprises values of said rate of change previously measured for said muscle.

6. A method according to claim 1, wherein said normalized index comprises predetermined values of said rate of change.

* * * * *